(12) United States Patent
Clor

(10) Patent No.: US 7,387,512 B2
(45) Date of Patent: Jun. 17, 2008

(54) ORTHODONTIC CORRECTION DEVICE

(76) Inventor: Charles Clor, 3, Chemin Bachmatten, 68150 Ostheim (FR)

( * ) Notice: Subject to any disclaimer, the term of this patent is extended or adjusted under 35 U.S.C. 154(b) by 0 days.

(21) Appl. No.: 11/245,966

(22) Filed: Oct. 11, 2005

(65) Prior Publication Data

US 2006/0204917 A1 Sep. 14, 2006

(30) Foreign Application Priority Data

Mar. 14, 2005 (FR) .................................. 05 50651

(51) Int. Cl.
*A61C 3/00* (2006.01)
(52) U.S. Cl. .......................................... 433/11; 433/10
(58) Field of Classification Search .................. 433/11, 433/8–9

See application file for complete search history.

(56) References Cited

U.S. PATENT DOCUMENTS 6,554,612 B2 * 4/2003 Georgakis et al. ............ 433/11
6,663,385 B2 * 12/2003 Tepper ........................ 433/11

* cited by examiner

*Primary Examiner*—Cris Rodriguez
*Assistant Examiner*—Candice C Stokes
(74) *Attorney, Agent, or Firm*—Egbert Law Offices

(57) ABSTRACT

Orthodontic correction device includes a locking device for an arch in the form of a bracket in which is provided for a groove aimed at co-operating with the arch. The groove includes a blocking device for the arch in the form of at least one pin extending at least partly above the groove at the level of the opening of the said groove. The opening is shaped so as to allow, during the insertion of the arch into the groove, passing around the pin.

8 Claims, 2 Drawing Sheets

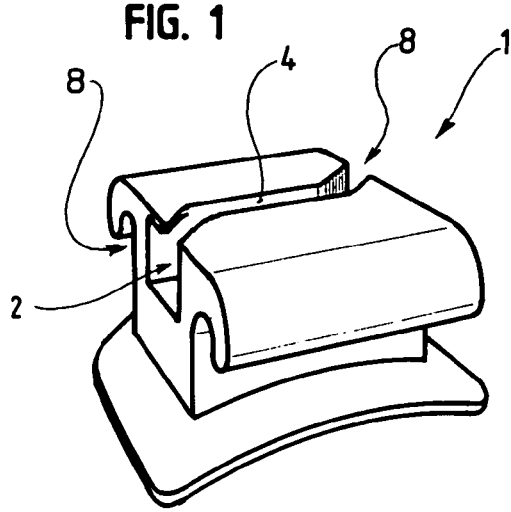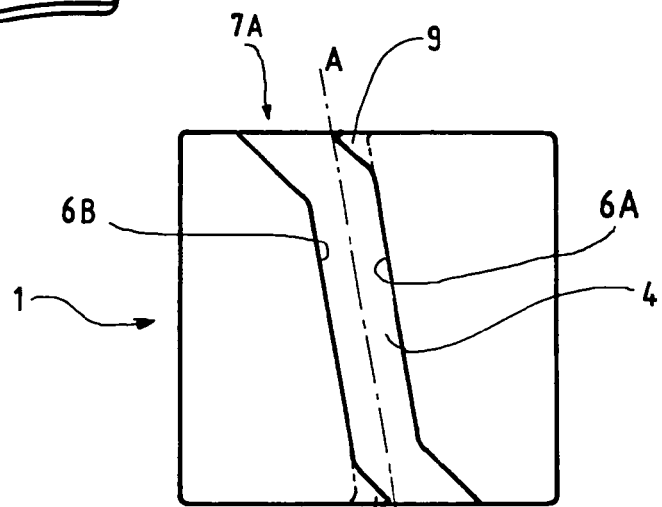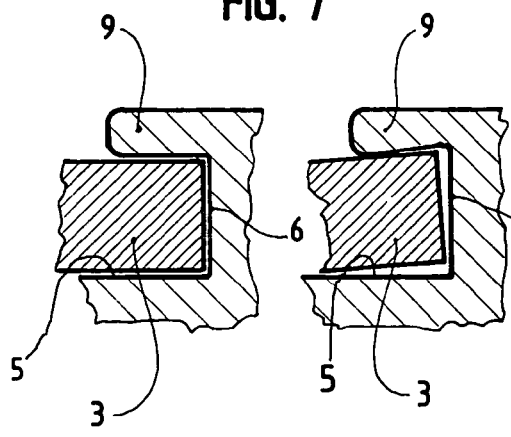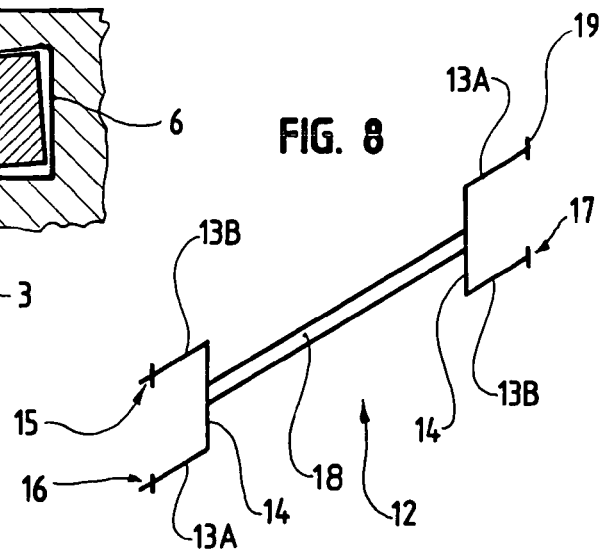

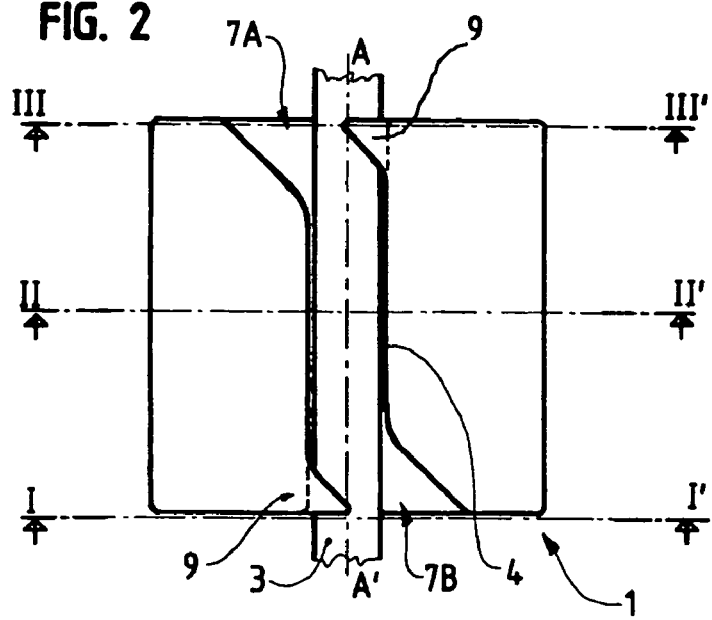
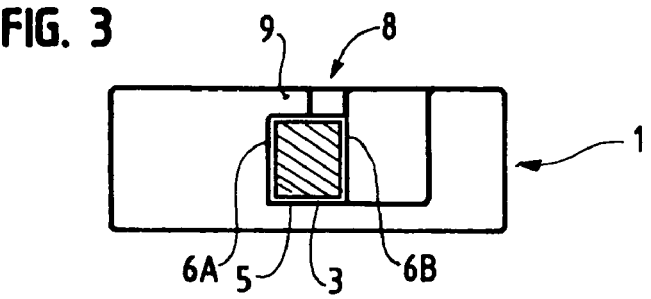
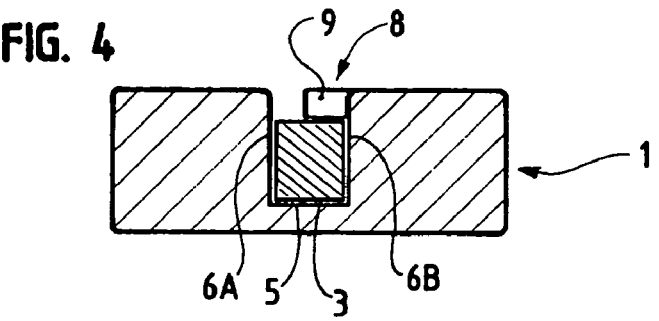
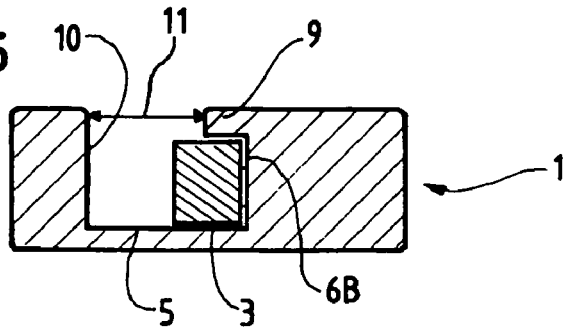

ORTHODONTIC CORRECTION DEVICE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention is related to the field of orthodontics, in particular to the field of the orthodontic clamps, commonly referred to as brackets.

BACKGROUND OF THE INVENTION

The orthodontic clamps or brackets are used in orthodontics in tooth-alignment correction devices. A bracket is an element aimed at being fixed through gluing to the front face, and sometimes to the back face, of each tooth, in order to serve as a clamp for an arch. This arch is usually rigid or shape memorizing, made out of metal. This arch is fixed to each bracket, generally at the level of a groove provided for in the latter. The cross-section of this arch can be designed round, square or rectangular.

The problem experienced with such a device resides in maintaining the arch in the groove of each bracket so as to prevent it from being released from it. The devices of the state of the art comprise various means for maintaining the arch in place in said groove.

One device contemplates maintaining the arch by placing a metal binding, in the form of a metal wire, or made out of synthetic material, in the form of a rubber band, on the bracket, through securing tabs. These securing tabs are made on both sides of said groove and on the outer walls of said bracket, arranged on the occlusal and gingival sides of the bracket, so that the binding is fixed to it to close the groove and to block the arch in the latter. However, a drawback resides in that the binding can be released, in particular when brushing the teeth, and may eventually damage the gum in the case of the metal wire, or may even be swallowed. Moreover, the metal wire is twisted and bent at its ends, thus being able to nip or irritate the mucosa through friction in the event it suddenly moves. The rubber bands lose their quality quickly and become dirty depending on the saliva and on the food habits, resulting into an even less aesthetic aspect of the bracket, and it is thus necessary to change them regularly. Finally, a metal or elastic binding requires a placing and replacing technique and time.

In order to cope with these drawbacks, some devices are provided with mechanical means for automatically locking the groove. These automatic locking means comprise a removable part aimed at co-operating with the bracket. This part can be in the form of a hinge articulated on said bracket or of a member coupled through snapping on or the like.

A device comprising a removable part articulated through a hinge has the drawback of being complex as regards the manufacture of the bracket. Moreover, the hinge is fitted on an axis or a pivot likely to be released or even to break.

A known snap-on locking device comprises a bracket the base of which aimed at being glued to the tooth is fixed to an upper portion in which the groove aimed at receiving the arch is provided for. On the side walls of the groove and on both sides of the latter are provided for one or two side grooves aimed at receiving a removable member, the member covering the upper opening of said groove being aimed at blocking the arch in the latter. In particular, according to a particular embodiment, the removable member is in the form of a metal arch having elastic characteristics so that it is deformed during its installation and that it recovers its original shape in locked position, the longitudinal edges of the member co-operating with the side walls of the groove.

Moreover, securing tabs remain present in order to add an elastic or metal binding, if necessary.

Even though this type of device does not use an elastic or metal binding, it has however the drawback of having a removable member having the above-mentioned drawbacks, in particular, it is likely to be released.

Moreover, a removable or articulated member has a backlash that can gradually increase. Finally, the shape of a bracket supporting a removable or articulated member is complex, thus increasing its design and its manufacturing cost.

BRIEF SUMMARY OF THE INVENTION

The purpose of the invention is to cope with the drawbacks of the state of technique while omitting the use of a rubber band or a metal wire as well as of a removable member. Moreover, the orthodontic device according to the invention remains simple to be manufactured and cheaper.

The orthodontic correction device according to the invention comprises means for locking an arch in the form of a bracket in which is provided for a groove aimed at co-operating with said arch, and it is mainly characterized in that said groove comprises means capable of blocking said arch, which means are in the form of at least one pin extending at least partly above said groove at the level of the opening of the latter, and in that said opening is shaped so as to allow, during the insertion of said arch into said groove, passing around said pin.

According to an additional feature of the device according to the invention, the blocking means are in the form of at least one pin formed by the extension of the edge of the wall which delimits the opening of access to the groove.

According to another additional feature of the device according to the invention, the blocking means are positioned at an end of the groove.

According to another additional feature of the device according to the invention, the opening through which the arch is inserted comprises in front of each or of all the pins a cut-out provided to allow the passing through of the arch during its installation, said cut-out having a shape complementary to that of said pin.

According to another additional feature of the device according to the invention, the blocking means comprise two pins, each one arranged on one of the longitudinal edges of the groove and oriented in an opposite direction to each other.

According to another additional feature of the device according to the invention, the lower face of the pin has a slope, so that its end is closer to the bottom of the groove, so as to increase the hold of the arch in said groove.

According to another additional feature of the device according to invention, the pin or pins are designed shearable.

The present invention also relates to a device for placing an arch on a correction device according to the invention. It is mainly characterized in that it comprises means capable of placing and removing said arch in the groove of the bracket by tilting this arch so that it can be inserted between the pin and the cut-out of the blocking means.

According to an additional feature, the device for placing an arch on a correction device, according to the invention, the means for placing and removing the arch, comprise at least one arm, preferably two, the ends of which are shaped so as to seize and curve the arch on both sides of the bracket and, according to whether one wishes to place or and to remove said arch, for pushing or pulling said arch, respectively.

Other features and advantages of the invention will become clear when reading the following detailed description of non-restrictive embodiments of the invention, with reference to the attached figures.

BRIEF DESCRIPTION OF THE SEVERAL VIEWS OF THE DRAWINGS

FIG. 1 is a schematic perspective view of a device according to the invention.

FIG. 2 is a top plan view of a device according to an embodiment of the invention.

FIG. 3 is a cross-sectional view according to the axis I-I' of FIG. 2.

FIG. 4 is a cross-sectional view according to the axis II-II' of FIG. 2.

FIG. 5 is a cross-sectional view according to the axis III-III' of FIG. 2.

FIG. 6 is a schematic top view of a device according to another embodiment of the invention.

FIG. 7 is a cross-sectional view of a detail of two embodiments 7A and 7B of the device according to the invention.

FIG. 8 is a schematic view of a particular embodiment of the device for installing the device according to the invention.

DETAILED DESCRIPTION OF THE INVENTION

The present invention relates to an orthodontic correction device 1, in particular a tooth-alignment correction device.

Such an orthodontic correction device 1 is commonly in the form of means for locking an arch 3, such as a bracket, as can be seen in FIG. 1, and aimed at being fixed through gluing to the front or back face of a tooth.

This bracket comprises means 2 capable of accommodating the arch 3, such as a groove 4 passing through the bracket. In particular, the arch 3, once it has been placed, rests on the bottom of the groove 4. The latter is delimited by a bottom 5 and two longitudinal edges 6A and 6B. It extends longitudinally with respect to the bracket, from an end 7A to an end 7B, the arch 3 emerging through each one of the ends 7A and 7B.

In this respect, the arch 3 is made of a metal wire having elastic shape-memory characteristics. It can have a round, square or rectangular cross-section, so that it acts on the bottom 5 and the edges 6 of groove 4 according to the torque and the angulation of the groove 4. This constraint is reflected, through the groove 4, on the bracket, in order to straighten the tooth on which it is mounted.

A feature of the invention resides in that the groove 4 comprises means 8 capable of blocking the arch 3 when it is positioned on the bottom of the groove 4. These blocking means 8 impede the arch 3 from leaving the groove 4 by extending at least partly above the latter. These blocking means 8 can be in the form of at least one pin 9. The latter can be formed of the extension of the surface of the correction device 1, preferably protruding with respect to at least one of the longitudinal edges 6.

The pin 9 is protruding and extends substantially perpendicularly with respect to the longitudinal edge 6A (or 6B), so as to be overhanging over the groove 4 in which rests the arch 3. The latter is blocked, on the one hand, laterally by the opposite longitudinal edge 6B (or 6A, respectively) and at the top through the pin 9.

The lower surface of the pin 9 is designed substantially orthogonal to the longitudinal edge 6A (or 6B) it extends. In a particular embodiment, which can be seen in FIG. 7, this surface can be designed skew, in order to better hold the arch in the groove 4, whereby the angle formed by the surface and the longitudinal edge can be smaller than 90°.

In the preferred embodiment of the device according to the invention, which can be seen in FIGS. 1 to 6, the blocking means 8 are located at the level of the ends 7A, 7B of the groove 4 and comprise two pins 9, each one being located at an end 7. According to another embodiment of the invention, the blocking means 8 can be in the form of one single pin 9 located along the groove 4, preferably substantially in the center of the latter.

The blocking means 8 comprise, in front of the pin 9, at least one cut-out 10 provided for in the opposite longitudinal edge 6A (or 6B) with respect to the edge 6B (or 6A, respectively) supporting the pin 9. This cut-out 10 has a shape complementary to that of the pin 9, so that it allows, through an opening 11 provided for between it and the pin 9, the passing through of the arch 3 during its placing by passing around the pin 9.

In this respect, the opening 11 is at least equal to the cross-section of the arch 3, so that the latter can be inserted between the pin 9 and the cut-out 10. Moreover, since this opening 11 is oblique with respect to the axis A-A' of the groove 4, it is necessary to impart a light bending to the arch 3, in order to place it while passing around the pin 9, so that the latter, under the action of the springy restoring of the arch 3, positions itself on the bottom of the groove 4, under the pin 9 and against the longitudinal edge 6A or 6B supporting the latter. Finally, when placing the arch 3 in the groove 4, the blocking means 8 extend at least partly above the groove and provide the opening 11 so shaped as to allow passing around the pin 9. This passing around occurs through a bending of the arch 3.

In the case of blocking means 8 comprising 2 pins 9A, 9B, the latter are each arranged on a longitudinal edge 6A (or 6B) opposite each other and are protruding in opposite direction with respect to each other. This particular arrangement provides high safety as to the holding of the arch 3. Indeed, if the arch 3 is shifted in one direction at the level of a pin 9A (or 9B), it remains blocked at the level of the opposite pin 9B (or 9A, respectively).

Moreover, the pin 9 can have a degree of overlapping of the arch 3 varying depending on the bracket and/or the correction to be performed. Thus, this degree of overlapping can be smaller than, equal to or larger than the cross-section of the arch 3.

The correction device 1 according to the invention offers the advantage of not requiring inserted parts or a removable or articulated part with respect to the bracket. Moreover, the design of such a device 1 is considerably facilitated and cheaper. No elastic or metal binding is now necessary for maintaining the arch 3 in place.

It should be noted that it can be contemplated that the pins 9 are designed shearable, thus allowing a rigid arch to be used at the end of the treatment.

It should also be noted, as can be seen in FIG. 1, that the bracket comprises externally, on the gum side and on the occlusal side, tabs aimed at allowing the passing through of a binding, if necessary.

The present invention also relates to a device 12 for placing an arch 3 on a correction device 1, in particular for placing the bracket in the accommodating means 2. Such a device for placing 12, as can be seen in FIG. 8, comprises means capable of placing and removing the arch 3 in the groove 4 of the bracket through inclining this arch 3 so that it can pass around the pin 9 and be inserted into the opening provided for between the pin 9 and the cut-out 10 of the blocking means 8. In particular, the means for placing and removing the arch 3 comprise two arms 13A, 13B extending parallel to each other and made integral, at one of their ends, by a transverse bar 14, and the free ends of which are provided with means 16 or 17, depending on whether they are capable of placing or removing the arch 3 of the bracket, respectively.

In particular, such a device 12 for placing and extracting an arch 3 can be mounted double, in order to allow placing the arch 3 on one side through placing means 16 and its extraction on the other side through the means 17, both means 16 and 17 being connected to each other by a rod 18.

In a particular embodiment, the placing means 16 comprise, on each one of the arms 13A and 13B, coupling members 15, which each consist of a transverse bar providing the ends of the arms 13A and 13B with the shape of a cross, in order to allow, on the one hand, clamping the arch 3 in order to exert a torsion and, on the other hand, exerting a thrust on this arch 3.

The removing means 17 also each comprise a transverse bar 19 providing the ends of the arms 13A and 13B with a T-shape, such as to allow them to pass behind the arch 3 placed in the groove 4, to twist it in order to pass around the pin 9, and to extract it from the groove 4.

Thanks to this placing device, the installation of an arch 3 on a correction device 1 according to the invention is largely facilitated and, hence, the installation time is reduced.

An advantage resides in the improvement of the sliding mechanics of the arch 3 and in the reduction of the forces exerted on the latter and on the teeth. This optimization of the forces results from the possibility for the arch 3 to freely slide in the groove 4, thus reducing the constraints.

The correction device 1 according to the invention is the more advantageous as it can indifferently be made out of metal, ceramics or any other adequate material.

Another advantage of this correction device 1 resides in that it can be adapted to any type of existing orthodontic clamp or to any kind of correction technique used.

I claim:

1. An orthodontic correction device comprising:
    an arch having a desired flexibility; and
    a bracket having a groove formed into a facing surface of said bracket, said arch received in said groove, said bracket having means thereon for releasably retaining said arch in said groove, said means being at least one pin extending from one side of said groove over a portion of said groove, the pin being flush with said facing surface of said bracket, the pin defining a space with an opposite side of said groove, said pin extending for less than a length of said groove, the flexibility of said arch being suitable so as to allow said arch to pass through said space and around said pin during an insertion of said arch into said groove, said bracket having a cut-out formed in a wall of said groove at said opposite side of said groove, said cut-out having a shape corresponding to a cross-sectional shape of said arch.

2. The device of claim 1, said pin being integral with said facing surface of said bracket.

3. The device of claim 1, said pin being positioned on at least one end of said groove.

4. The device of claim 1, said means comprising a pair of pins positioned respectively at opposite ends of said groove, one of said pair of pins facing in an opposite direction to the other of said pair of pins.

5. The device of claim 1, the pin having a sloped lower face so as to extend toward a bottom of said groove.

6. The device of claim 1, said pin being shearably connected to said bracket.

7. The device of claim 1, further comprising:
    a means for placing and removing said arch from said groove insertable between the pin and said cut-out.

8. The device of claim 7, said means for placing and removing comprising at least one arm having ends shaped so as to seize and curve said arch on opposite sides of said bracket.

* * * * *